(12) United States Patent
Watson et al.

(10) Patent No.: US 8,370,080 B2
(45) Date of Patent: Feb. 5, 2013

(54) METHODS AND SYSTEMS FOR DETERMINING WHETHER TO TRIGGER AN ALARM

(75) Inventors: James Nicholas Watson, Dunfermline (GB); Paul Stanley Addison, Edinburgh (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 959 days.

(21) Appl. No.: 12/249,632

(22) Filed: Oct. 10, 2008

(65) Prior Publication Data

US 2010/0016691 A1 Jan. 21, 2010

Related U.S. Application Data

(60) Provisional application No. 61/080,797, filed on Jul. 15, 2008.

(51) Int. Cl.
*G01N 33/49* (2006.01)
*G06F 15/00* (2006.01)
*G11C 17/00* (2006.01)

(52) U.S. Cl. .................... 702/24; 700/1; 365/94
(58) Field of Classification Search ............... None
See application file for complete search history.

(56) References Cited

U.S. PATENT DOCUMENTS

| | | | |
|---|---|---|---|
| 4,289,141 A | 9/1981 | Cormier |
| 5,319,355 A | 6/1994 | Russek |
| 5,353,799 A | 10/1994 | Chance |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod |
| 5,827,195 A | 10/1998 | Lander |
| 5,846,190 A | 12/1998 | Woehrle |
| 5,967,995 A | 10/1999 | Shusterman et al. |
| 6,002,952 A | 12/1999 | Diab et al. |
| 6,036,653 A | 3/2000 | Baba et al. |
| 6,094,592 A | 7/2000 | Yorkey |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,360,114 B1 | 3/2002 | Diab et al. |
| 6,361,501 B1 | 3/2002 | Amano et al. |
| 6,393,311 B1 | 5/2002 | Edgar, Jr. et al. |
| 6,449,501 B1 | 9/2002 | Reuss |
| 6,510,329 B2 | 1/2003 | Heckel |
| 6,561,986 B2 | 5/2003 | Baura |
| 6,606,510 B2 | 8/2003 | Swedlow et al. |
| 6,606,511 B1 | 8/2003 | Ali et al. |
| 6,608,934 B2 | 8/2003 | Scheirer |
| 6,650,917 B2 | 11/2003 | Diab et al. |
| 6,654,623 B1 | 11/2003 | Kastle |
| 6,654,624 B2 | 11/2003 | Diab et al. |
| 6,675,031 B1 | 1/2004 | Porges et al. |
| 6,699,194 B1 | 3/2004 | Diab et al. |
| 6,745,060 B2 | 6/2004 | Diab et al. |
| 6,771,994 B2 | 8/2004 | Kiani et al. |
| 6,810,277 B2 | 10/2004 | Edgar, Jr. et al. |
| 6,822,564 B2 | 11/2004 | Al-Ali |
| 6,826,419 B2 | 11/2004 | Diab et al. |
| 6,898,452 B2 | 5/2005 | Al-Ali et al. |
| 6,931,269 B2 | 8/2005 | Terry |
| 6,970,792 B1 | 11/2005 | Diab |
| 6,987,994 B1 | 1/2006 | Mortz |
| 6,993,377 B2 | 1/2006 | Flick et al. |
| 7,001,337 B2 | 2/2006 | Dekker |
| 7,006,856 B2 | 2/2006 | Baker, Jr. et al. |
| 7,020,507 B2 | 3/2006 | Scharf |
| 7,024,233 B2 | 4/2006 | Ali et al. |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung |
| 7,171,269 B1 | 1/2007 | Addison |
| 7,173,525 B2 | 2/2007 | Albert |
| 7,194,293 B2 | 3/2007 | Baker, Jr. |
| 7,203,267 B2 | 4/2007 | De Man et al. |
| 7,225,013 B2 | 5/2007 | Geva et al. |
| 7,254,500 B2 | 8/2007 | Makeig |

(Continued)

FOREIGN PATENT DOCUMENTS

| | | |
|---|---|---|
| JP | 09-084776 | 3/1997 |
| WO | WO 01/25802 | 4/2001 |
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul S., The Illustrated Wavelet Transform Handbook, Taylor & Francis Group, 2002.

(Continued)

*Primary Examiner* — John S Brusca

(57) ABSTRACT

According to embodiment, systems and methods for processing a physiological measurement and generating alarms based on the measurement are provided. Multiple features of a single physiological measurement may be concurrently monitored to generate alarms. One or more of the features may be based on a trend of the physiological measurement. One or more of the features may be based on a wavelet transform of the physiological measurement. Different features may be used in different combinations to lower the percentage of false alarms while still recognizing valid alarm events.

17 Claims, 11 Drawing Sheets

U.S. PATENT DOCUMENTS

| | | |
|---|---|---|
| 7,289,835 B2 | 10/2007 | Mansfield |
| 7,355,512 B1 | 4/2008 | Al-Ali |
| 7,457,652 B2 | 11/2008 | Porges et al. |
| 7,471,969 B2 | 12/2008 | Diab et al. |
| 7,477,571 B2 | 1/2009 | Melese et al. |
| 7,499,835 B2 | 3/2009 | Weber et al. |
| 7,515,949 B2 | 4/2009 | Norris |
| 7,519,488 B2 | 4/2009 | Fu |
| 7,523,011 B2 | 4/2009 | Akiyama et al. |
| 7,566,306 B2 | 7/2009 | Fujiwara et al. |
| 8,082,110 B2 | 12/2011 | Watson et al. |
| 2003/0163057 A1 | 8/2003 | Flick et al. |
| 2005/0043616 A1 | 2/2005 | Chinchoy |
| 2006/0122476 A1 | 6/2006 | Van Slyke |
| 2006/0209631 A1 | 9/2006 | Melese et al. |
| 2006/0211930 A1 | 9/2006 | Scharf et al. |
| 2006/0220881 A1 | 10/2006 | Al-Ali et al. |
| 2006/0226992 A1 | 10/2006 | Al-Ali et al. |
| 2006/0229519 A1 | 10/2006 | Fujiwara et al. |
| 2006/0238358 A1 | 10/2006 | Al-Ali et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0043269 A1 | 2/2007 | Mannheimer et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0208259 A1 | 9/2007 | Mannheimer |
| 2007/0282212 A1 | 12/2007 | Sierra et al. |
| 2008/0039699 A1 | 2/2008 | Neumann |
| 2008/0045832 A1 | 2/2008 | McGrath |
| 2008/0081971 A1 | 4/2008 | Ollerdessen |
| 2008/0082018 A1 | 4/2008 | Sackner et al. |
| 2008/0091092 A1 | 4/2008 | Al-Ali |
| 2008/0091093 A1 | 4/2008 | Al-Ali |
| 2008/0214903 A1 | 9/2008 | Orbach |
| 2008/0221418 A1 | 9/2008 | Al-Ali et al. |
| 2008/0242955 A1 | 10/2008 | Uutela et al. |
| 2008/0243021 A1 | 10/2008 | Causevic et al. |
| 2009/0326871 A1 | 12/2009 | Watson et al. |
| 2010/0079279 A1 | 4/2010 | Watson et al. |
| 2010/0081898 A1 | 4/2010 | Addison et al. |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Yamada, Michio, "Wavelet Analysis and Its Application," Journal of the Institute of Electronics, Information and Communication Engineers, vol. 76, No. 5, May 1993, pp. 518-528.

Non Final Office Action for U.S. Appl. No. 12/242,894 mailed on Feb. 27, 2012; 8 pages.

Non Final Office Action for U.S. Appl. No. 12/242,204 mailed on Jun. 18, 2012; 5 pages.

METHODS AND SYSTEMS FOR DETERMINING WHETHER TO TRIGGER AN ALARM

CROSS REFERENCE TO RELATED APPLICATION

This Application claims the benefit of U.S. Provisional Application No. 61/080,797, filed Jul. 15, 2008 which is hereby incorporated by reference herein in its entirety.

SUMMARY

The present disclosure relates to signal processing and, more particularly, the present disclosure relates to processing one or more signals to determine when to generate an alarm. The advantages of the Continuous Wavelet Transform (CWT), inherent resolution in both scale and time, may be used to identify and characterize features and their periodicities within a signal. Regions and amplitudes within the scalogram associated with these features may then be analyzed to identify, for example, patterns of desaturation in an oxygen saturation signal and to decide if it is appropriate to trigger an alarm.

For example if the original signal is the oxygen saturation signal of a subject, analysis of the signal might indicate whether a drop in the measured value is likely to be long term or merely a transient event (especially if the saturation value is derived using wavelet techniques where such changes in value are more accurately resolved in time). An alarm may then be triggered accordingly. For example if the saturation value is currently low but increasing or predicted to rise (e.g., by wavelet analysis, syntactic processing, adaptive processing or Baysean analysis) then an alarm may not trigger. However if the value is low and dropping, or predicted to drop in the future, an alarm may trigger.

Multiple features (e.g., either wavelet or conventional features such as slope, average, median, skew, etc.) may be considered in deciding if it is appropriate to trigger an alarm. For example, two or more features may be considered concurrently and in parallel in any practical implementation of this method.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
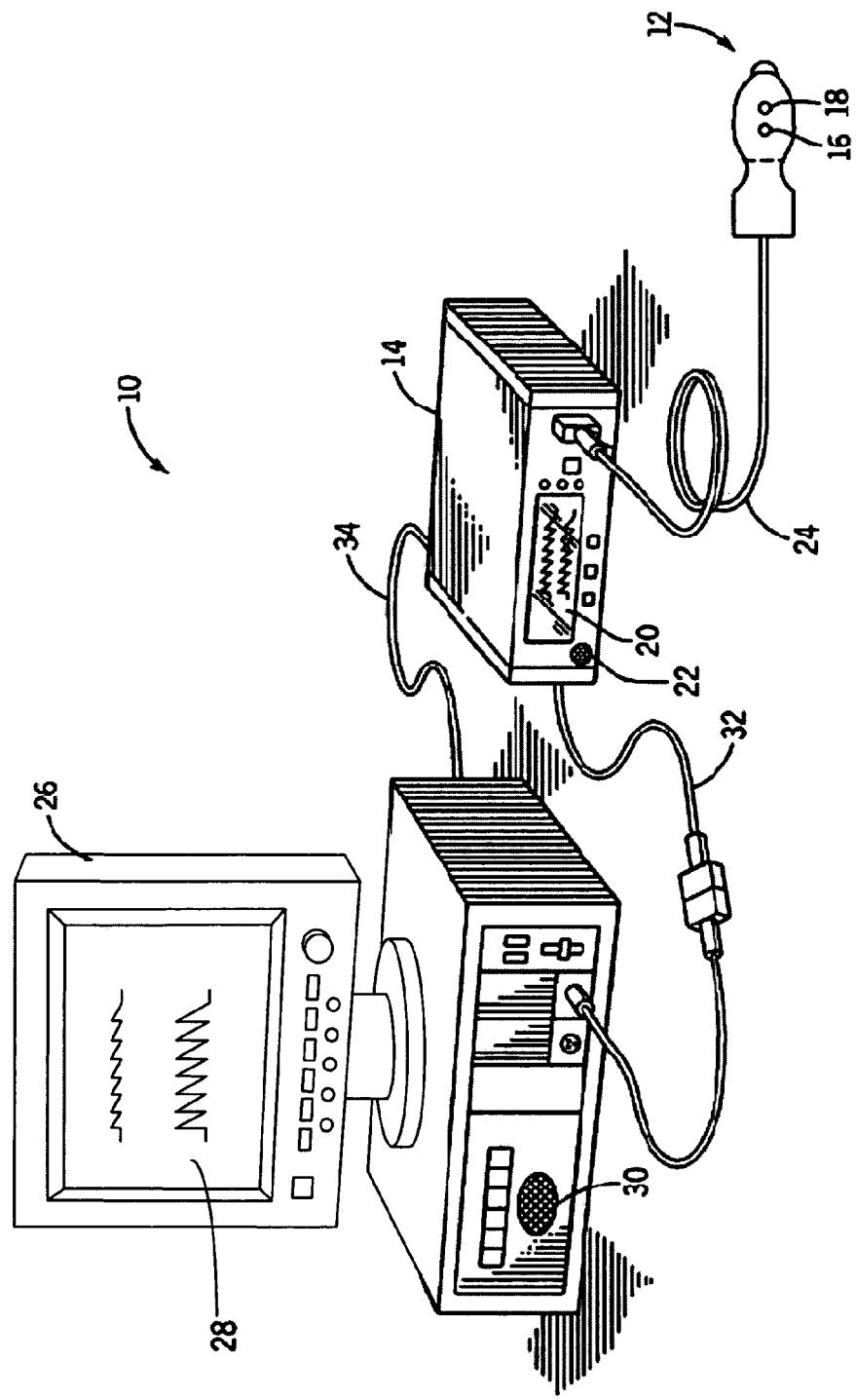
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patients blood (as opposed to measuring oxygen saturation directly by analyzing a blood sample taken from the patient) and changes in blood volume in the skin. Ancillary to the blood oxygen saturation measurement pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time may be referred to as the photoplethysmogram (PPG) signal. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda)+(1-s)\beta_r(\lambda))/(t)) \quad (1)$$

where:
$\lambda$=wavelength;
t=time;
I=intensity of light detected;
$I_o$=intensity of light transmitted;
s=oxygen saturation;
$\beta_o, \beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_R)}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
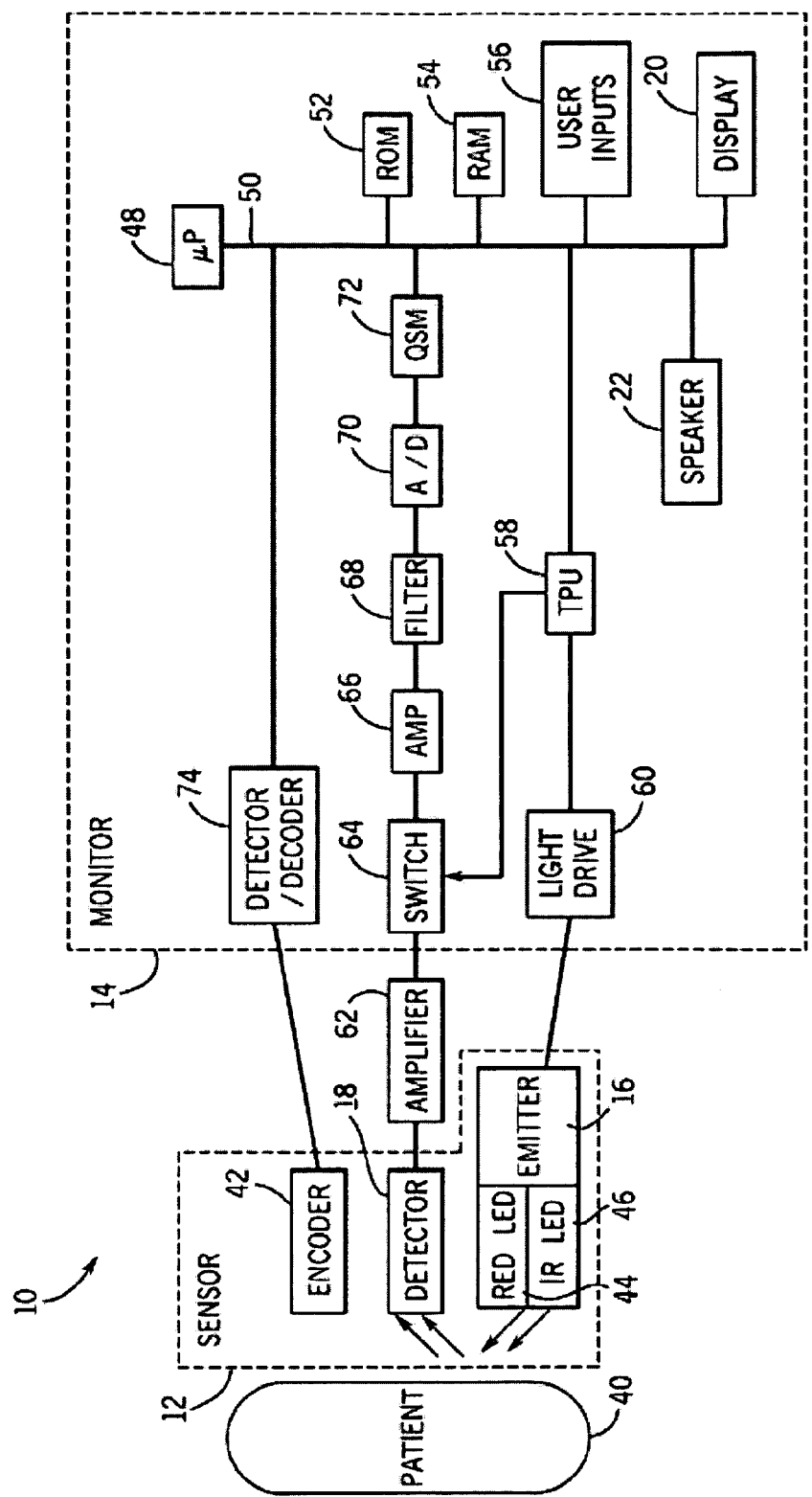
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40. An example of a device configured to perform such calculations is the Model N600x pulse oximeter available from Nellcor Puritan Bennett LLC.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as SpO₂ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise and motion artifacts, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Motion artifact can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right)dt \tag{9}$$

where ψ*(t) is the complex conjugate of the wavelet function ψ(t), a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of multiple wavelets (e.g., on the order of tens, hundreds, thousands, or any other number) that are each scaled in accordance with scales of interest of a signal such that smaller scale components of a signal are transformed using wavelets scaled more compactly than wavelets used to extract larger scale components of the signal. The window size of data to which each wavelet gets applied varies according to scale as well. Thus, a higher resolution transform is possible using continuous wavelets relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '||' is the modulus operator. The scalogram may be rescaled for useful purposes. One common rescaling is defined as $$S_R(a,b) = \frac{|T(a,b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \qquad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2}. \qquad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
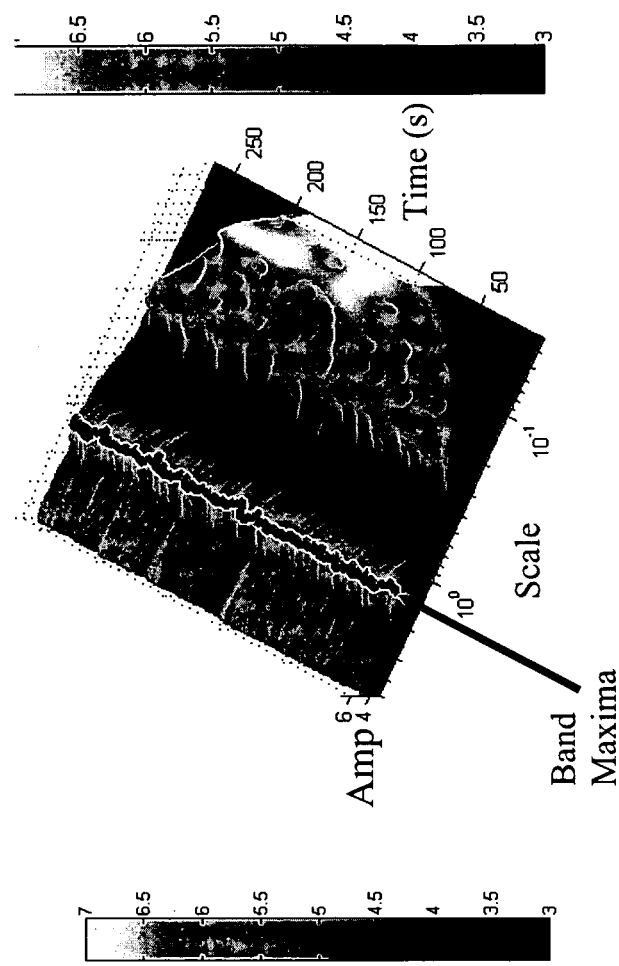
FIGS. 3(a) and 3(b) show illustrative views of a scalogram derived from a PPG signal in accordance with an embodiment.
Figure 3A:
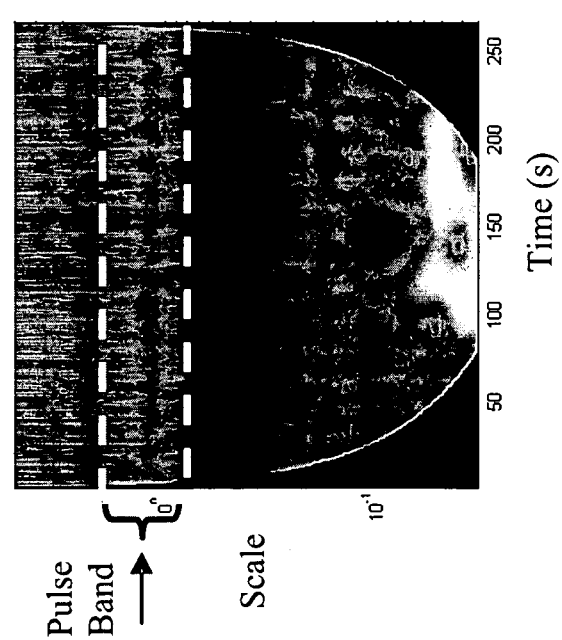

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
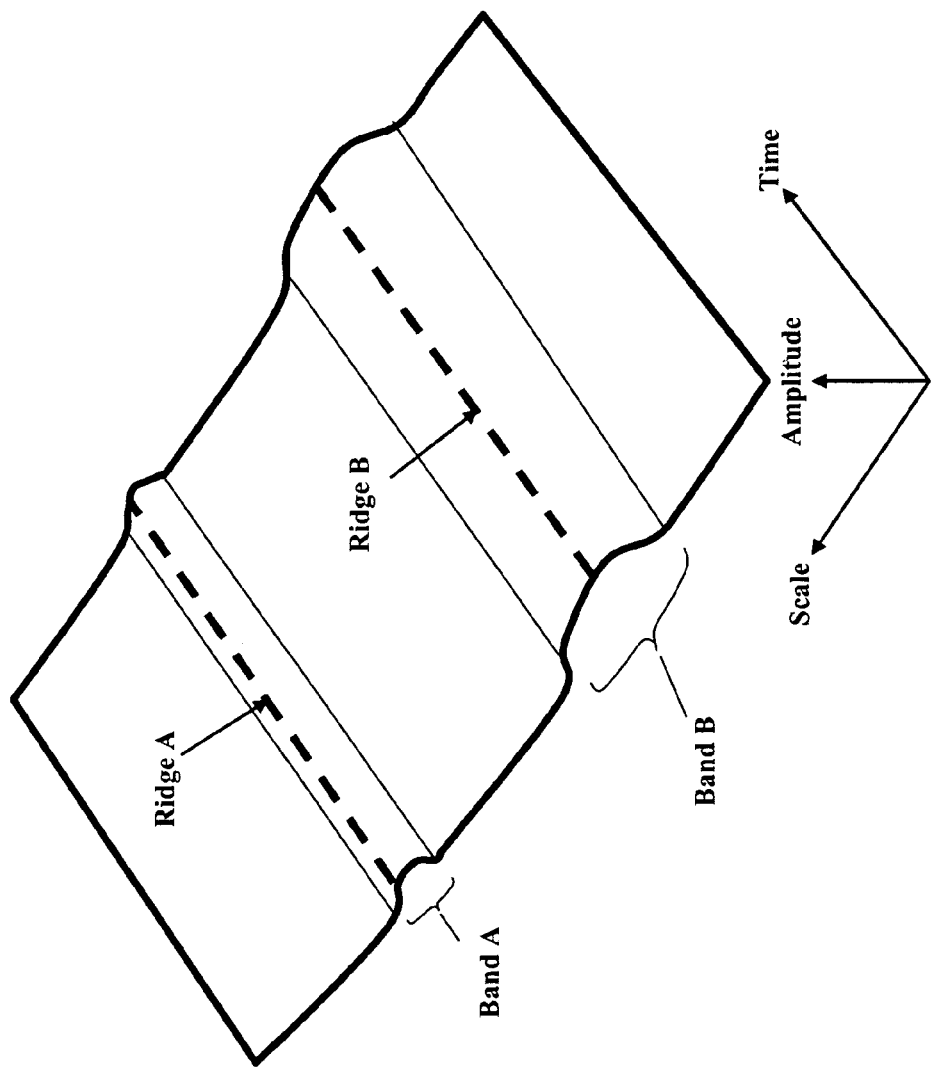
FIG. 3(c) shows an illustrative scalogram derived from a signal containing two pertinent components in accordance with an embodiment.
Figure 3D:
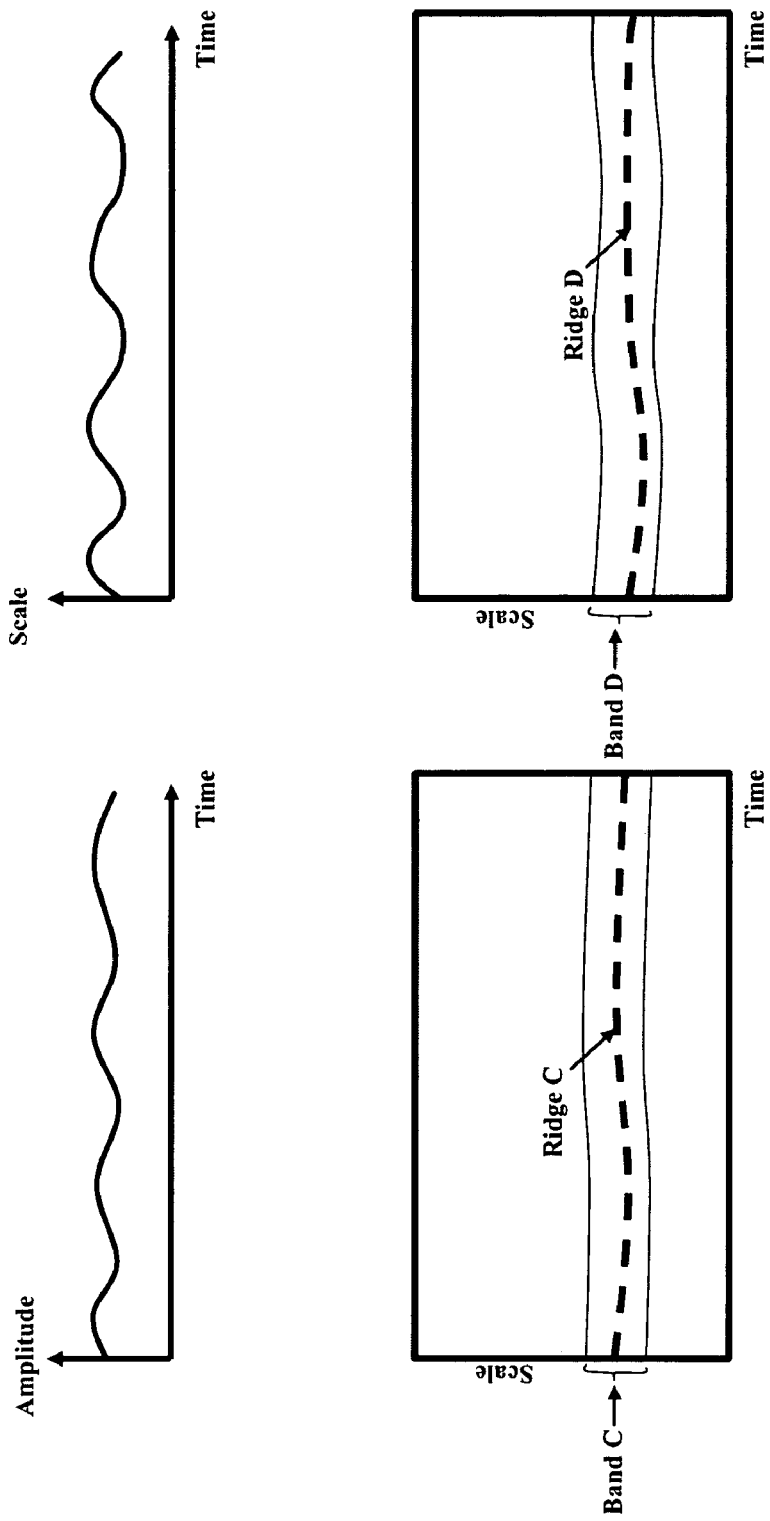
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g}\int_{-\infty}^{\infty}\int_0^{\infty} T(a,b)\frac{1}{\sqrt{a}}\psi\left(\frac{t-b}{a}\right)\frac{da\,db}{a^2} \quad (15)$$

which may also be written as:

$$x(t) = \frac{1}{C_g}\int_{-\infty}^{\infty}\int_0^{\infty} T(a,b)\psi_{a,b}(t)\frac{da\,db}{a^2} \quad (16)$$

where $C_g$ is a scalar value known as the admissibility constant. It is wavelet type dependent and may be calculated from:

$$C_g = \int_0^{\infty}\frac{|\hat{\psi}(f)|^2}{f}df \quad (17)$$

Figure 3E:
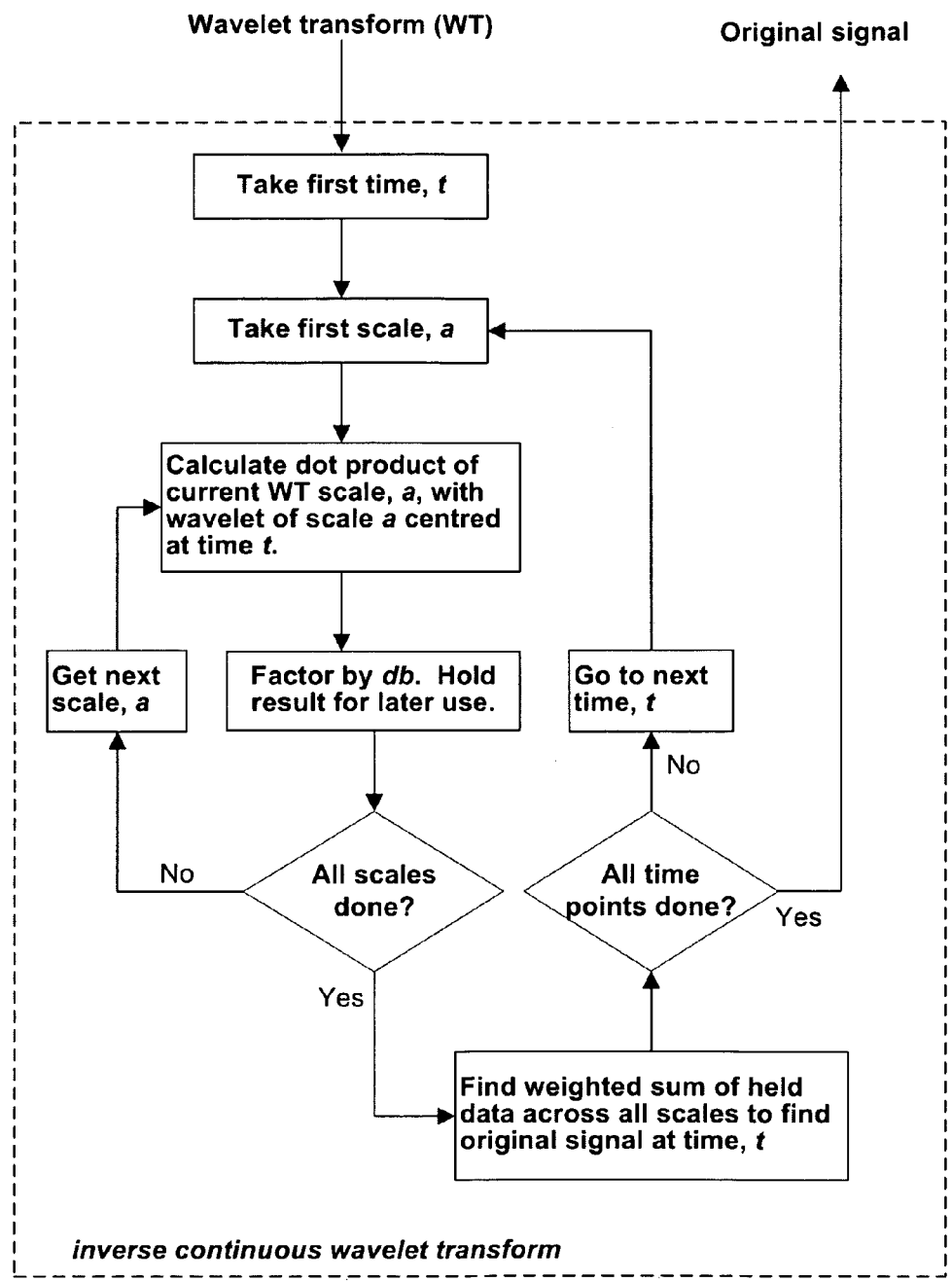
FIGS. 3(e) and 3(f) are flow charts of illustrative steps involved in performing an inverse continuous wavelet transform in accordance with an embodiment.
Figure 3F:
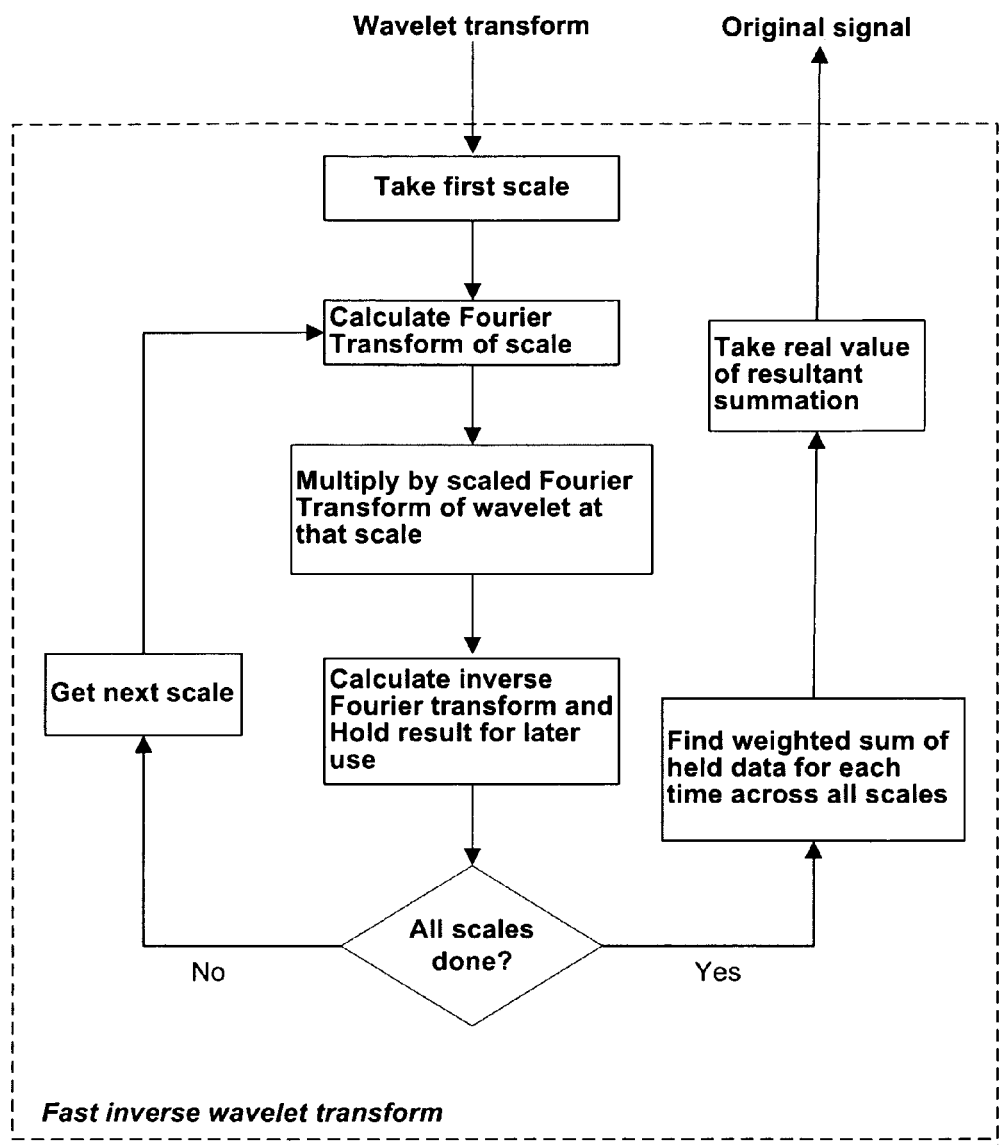

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
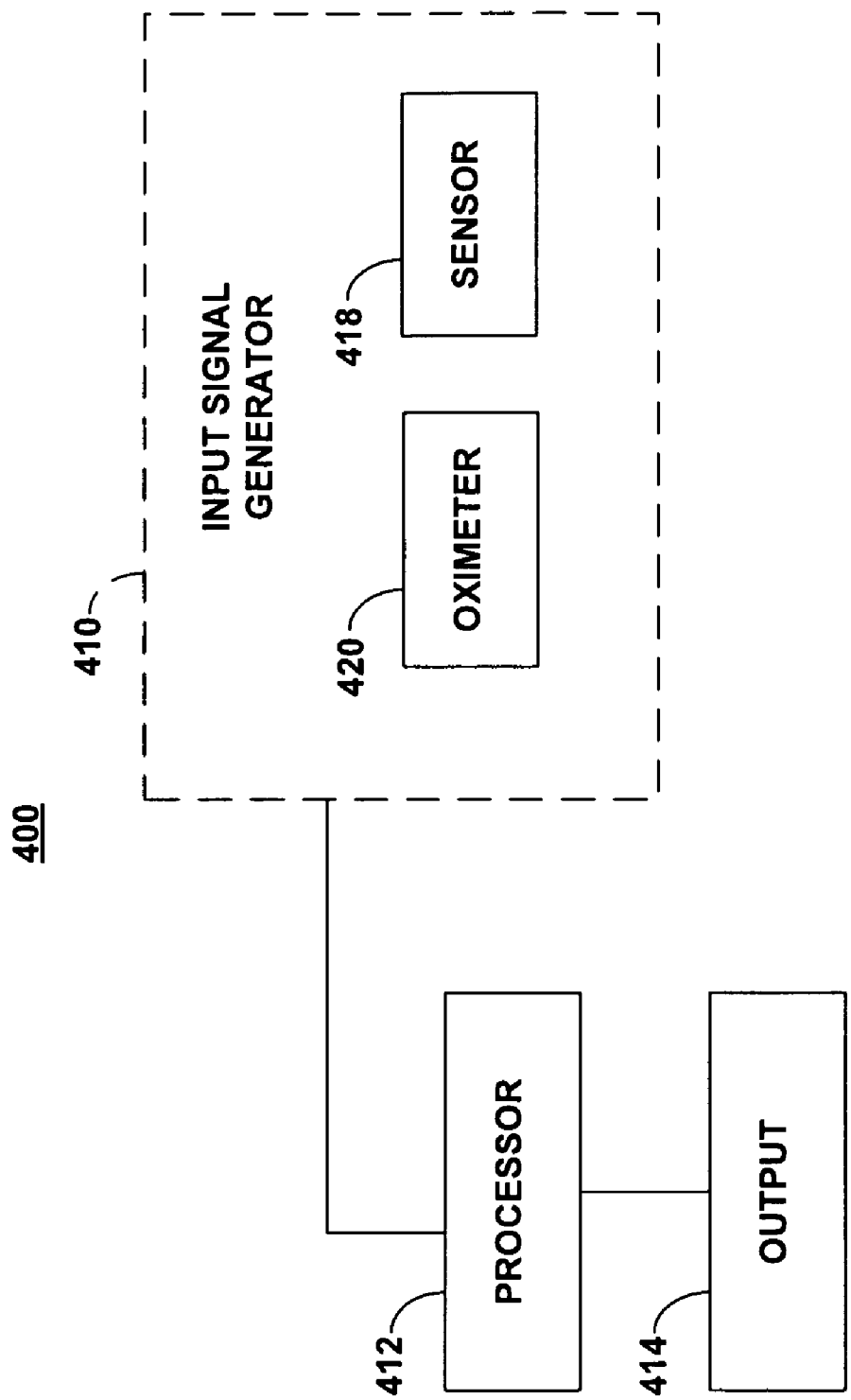
FIG. 4 is a block diagram of an illustrative continuous wavelet processing system in accordance with an embodiment.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

In an embodiment, a continuous wavelet processing system or processor (e.g., processor 412) may generate an $SpO_2$ signal or trend using a PPG signal. The $SpO_2$ signal or trend may, for example, be derived from a wavelet ratio surface, from a Lissajous figure, or both as more fully discussed in U.S. Patent Publication No. 2006/0258921, which is hereby incorporated by reference herein in its entirety. Any other suitable technique for determining $SpO_2$ signals or trends may be used such as any suitable time domain techniques (e.g., ratio of ratios discussed above).

In an embodiment, a wavelet processing system may process an $SpO_2$ signal or trend to determine if it is appropriate to trigger an alarm. For example, processor 412 in system 400 may generate an $SpO_2$ signal and analyze the signal to determine when a patient's blood oxygenation levels are at dangerous levels and/or showing a dangerous pattern. A system may process an $SpO_2$ signal based on two or more features of the signal. In an embodiment, a system may process an $SpO_2$ signal such that an alarm is generated if a moving average of the signal is below a threshold and the instantaneous slope of the signal is non-positive. Accordingly, false alarms are not generated when an $SpO_2$ signal's moving average is below a threshold but a slope (e.g., an instantaneous slope or a slope over a particular time period) of the signal indicates that it is increasing. By processing an $SpO_2$ signal according to multiple features, a system in accordance with the disclosure may generate fewer false alarms than a system that only analyzes an $SpO_2$ signal's amplitude.

Figure 5:
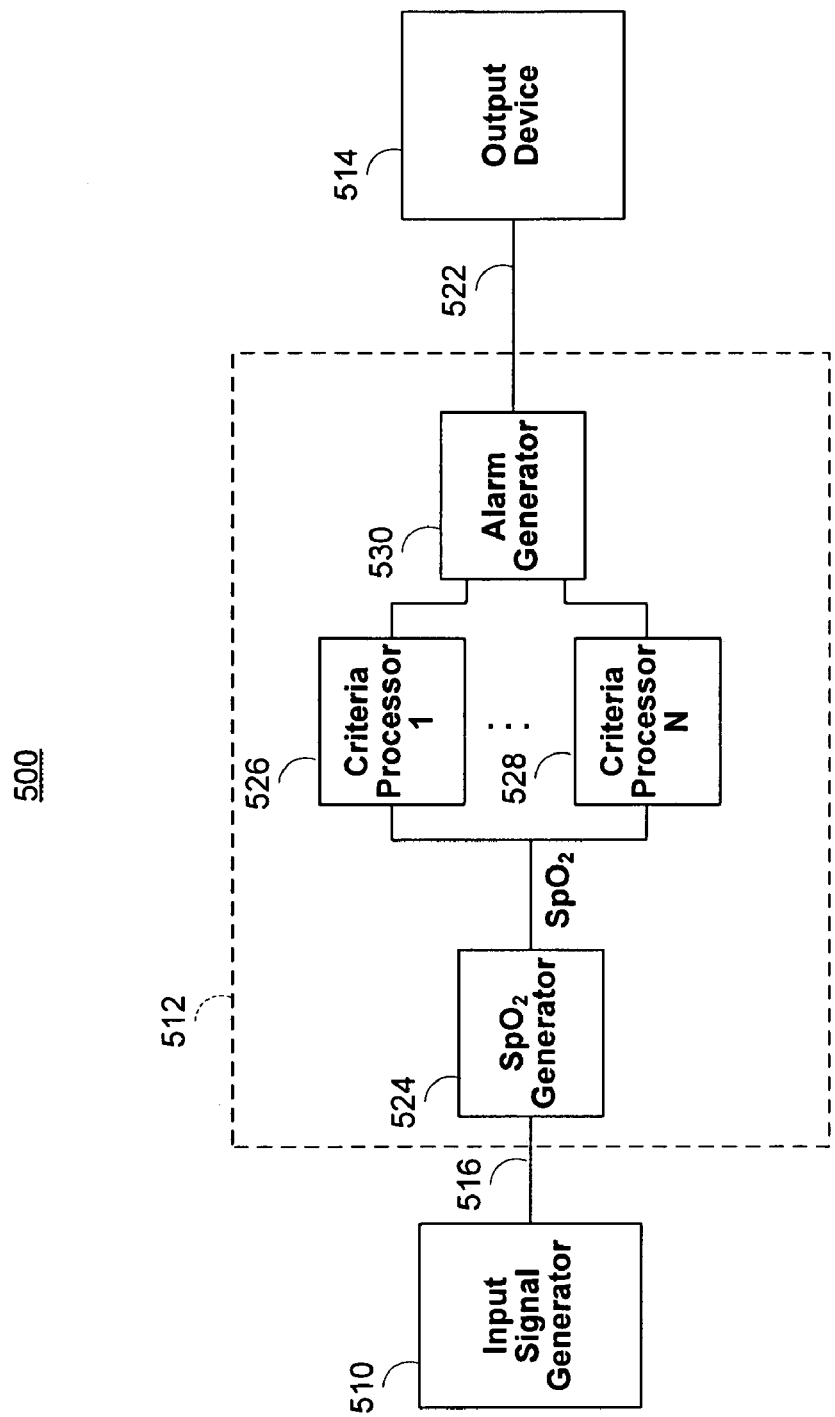
FIG. 5 is a block diagram of an illustrative continuous wavelet processing system in accordance with an embodiment.

FIG. 5 is an illustrative continuous wavelet processing system in accordance with an embodiment. In this embodiment, input signal generator 510 (or generator 410) may generate input signal 516 which may be a physiological signal (e.g., a PPG signal). Processor 512 (or processor 412) may analyze input signal 516 to generate alarm signal 522 that is read by output device 514 (or output device 414). Processor 512 may include an $SpO_2$ signal generator 524. $SpO_2$ signal generator 524 may generate an $SpO_2$ signal. Any suitable technique or combination of techniques may be used to generate an $SpO_2$ signal. Processor 512 may also include first criteria processor 526 and second criteria processor 528. Each criteria processor may analyze the $SpO_2$ signal and provide an output based on the $SpO_2$ signal. The output of first criteria processor 526 may indicate the value of a first characteristic of the $SpO_2$ signal, and the output of the second criteria processor 528 may indicate the value of a second characteristic of the $SpO_2$ signal. First criteria processor 526 and second criteria processor 528 may each indicate any suitable characteristic of an $SpO^2$ signal for determining if it is appropriate to trigger an alarm. For example, suitable characteristics may include instantaneous value, moving average, instantaneous slope, average slope, second derivative, and/or any other suitable characteristic, and/or any other combination of characteristics. While only two criteria processors are shown in FIG. 5, it is understood that any number of criteria processors may be used in accordance with the disclosure. Processor 512 may include alarm generator 530 to generate an alarm based at least in part on the output of first criteria processor 526 and second criteria processor 528. For example, alarm generator 530 may compare the output of first criteria processor 526 and second criteria processor 528 such that an alarm is generated only when the $SpO_2$ signal meets a combination of criteria.

In an embodiment, first criteria processor 526 may generate an $SpO_2$ signal's moving average. For example, first criteria processor 526 may be an integrator. By averaging the values of the $SpO_2$ signal, first criteria processor 526 may smooth the signal and remove any high-frequency noise. First criteria processor 526 may calculate a moving average using any suitable number of samples captured at any suitable sampling frequency. Second criteria processor 528 may generate a value corresponding to the $SpO_2$ signal's instantaneous slope. For example, second criteria processor 528 may be a slope detector. Second criteria processor 528 may determine the deference between a pair of samples to determine the $SpO_2$ signal's instantaneous slope. The value corresponding to the $SpO_2$ signal's instantaneous slope may provide information related to the current direction of the $SpO_2$ signals immediate movement. In an embodiment, second criteria processor 528 may generate a value corresponding to the $SpO_2$ signal's average slope. For example, the $SpO_2$ signal's slope may be averaged over multiple slope measurements to remove any high-frequency noise in the $SpO_2$ signal. In an embodiment, alarm generator 530 may compare the output of first criteria processor 526 and second criteria processor 528 such that an alarm is generated only when the $SpO_2$ signal's moving average is below a threshold and the $SpO_2$ signal's instantaneous slope is non-positive. In some embodiments, alarm generator 530 may also generate an alarm whenever the $SpO_2$ signal's slope is below a threshold (e.g., a relatively large negative number) regardless of the $SpO_2$ signal's moving average. In such embodiments, a preemptive alarm may be issued before the moving average ever goes below a threshold.

In an embodiment, processing an $SpO_2$ signal to generate an alarm may include processing the wavelet transform of the $SpO_2$ signal. A system may process an $SpO_2$ signal by calculating a wavelet transform (e.g., the continuous wavelet transform) of the signal, generating a scalogram, and then analyzing one or more features of the scalogram. For example, a system may calculate a wavelet transform of an $SpO_2$ signal and then analyze an RAP of the scalogram, an RSP of the scalogram, and/or any other suitable measurements of the scalogram, and/or any combination of measurements. Calculating a wavelet transform of an $SpO_2$ signal and analyzing a scalogram based on the wavelet transform may provide additional information about the $SpO_2$ signal or the patient's blood oxygenation levels.

Figure 6:
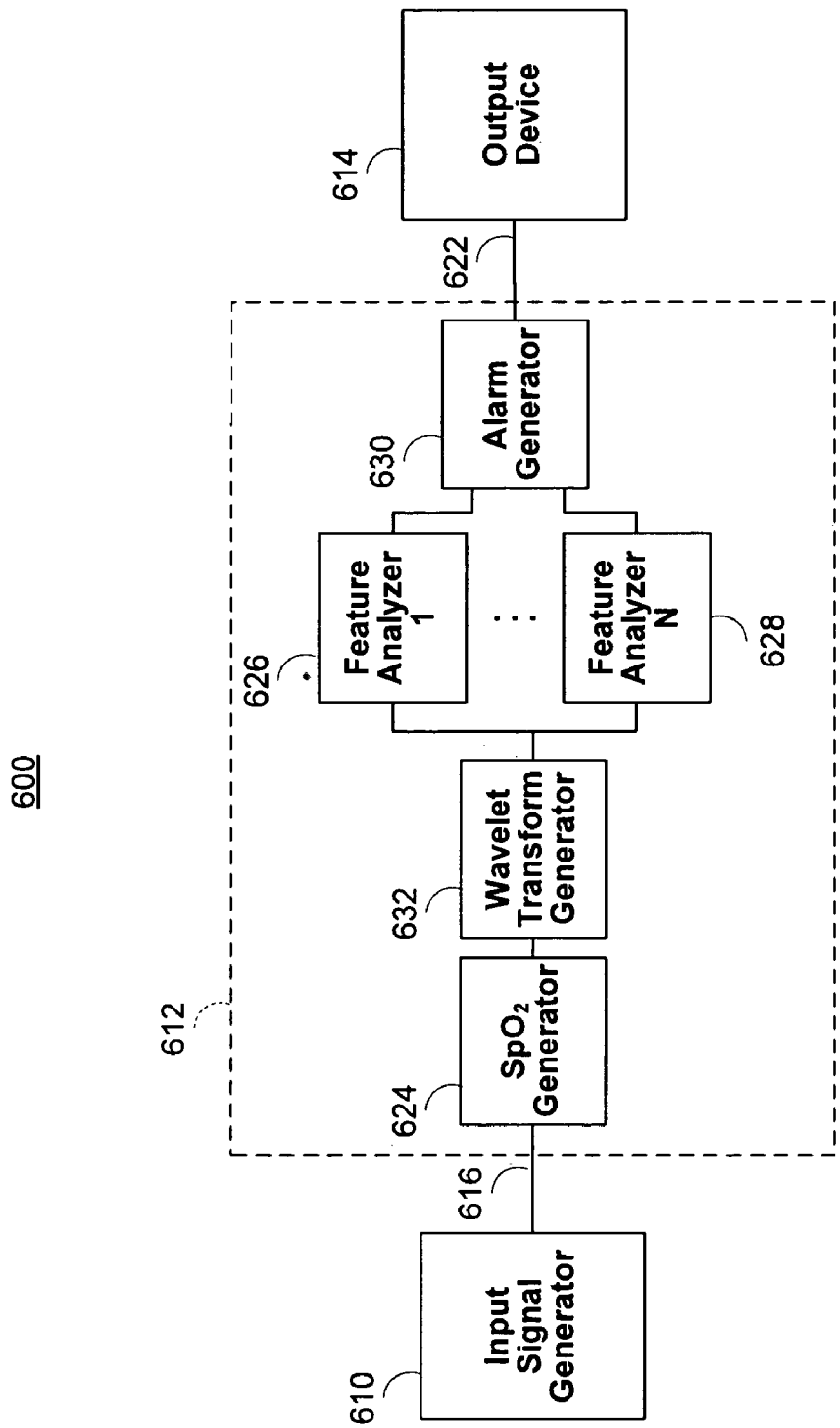
FIG. 6 is a block diagram of an illustrative continuous wavelet processing system in accordance with an embodiment.

FIG. 6 is an illustrative continuous wavelet processing system in accordance with an embodiment. In this embodiment, input signal generator 610 (or generator 410) may generate input signal 616 which may be a physiological signal (e.g., a PPG signal). Processor 612 (or processor 412) may analyze input signal 616 to generate alarm signal 622 that is read by output device 614 (or output device 414). Processor 612 may include an $SpO_2$ signal generator 624. $SpO_2$ signal generator 624 may generate an $SpO_2$ signal. As previously discussed, a variety of methods may be used to generate an $SpO_2$ signal. System 600 further includes wavelet transform generator 632 and feature analyzers 626 and 628. Wavelet transform generator 632 may calculate the wavelet transform of the $SpO_2$ signal from $SpO_2$ signal generator 624 such that feature analyzers 626 and 628 may analyze the wavelet transform or a scalogram based on the wavelet transform. While only two feature analyzers are shown in FIG. 6, it is understood that a system may include any number of features analyzers for processing a scalogram in accordance with the disclosure. Alarm generator 630 may then generate an alarm based at least in part on the output of feature analyzers 626 and 628.

Feature analyzers 626 and 628 may analyze any suitable scalogram features in parallel. For example, feature analyzers 626 and 628 may analyze amplitude at a particular scale, a moving average of the amplitude at a particular scale (i.e., an integration of the amplitude), a slope of the amplitude at a particular scale, a slope of the amplitude along a particular surface (e.g., line or ridge) of a scalogram, a slope of the amplitude between one or more averaged regions of a scalogram, the average amplitude across all scales, an RAP, a moving average of an RAP, a slope of an RAP, an average band amplitude perturbation (e.g., the average amplitude across a band), an RSP, a moving average of an RSP, a slope of an RSP, an average band scale perturbation (e.g., the average scale of a band), and/or any other suitable features, and/or any combinations thereof.

Alarm generator 630 may then decide if it is appropriate to trigger an alarm based on the outputs of feature analyzers 626 and 628. For example, alarm generator 630 may decide to trigger an alarm if feature analyzer 626 indicates that the value of an RAP is below a threshold and feature analyzer 628 indicates that the slope of an amplitude at a particular scale is decreasing. In accordance with the disclosure, alarm generator 630 may determine the appropriateness of triggering an alarm based on any combination of indicators from feature analyzers 626 and 628.

In one embodiment, alarm generator 630 may determine whether to trigger an alarm based at least in part on whether there is a significant deterioration in signal quality. Any suitable technique for determining signal quality may be used. For example, U.S. patent application Ser. No. 12/242,204, entitled "DETECTING A SIGNAL QUALITY DECREASE IN A MEASUREMENT SYSTEM," filed Sep. 30, 2008, which is hereby incorporated by reference herein in its entirety, discusses suitable techniques where, for example, signal-to-noise levels may be examined to determine if they fall below a suitable threshold.

In one embodiment, alarm generator 630 may determine whether to trigger an alarm based at least in part on whether there is a probe off condition. Any suitable technique for determining the existence of a probe off condition may be used. For example, U.S. patent application Ser. No. 12/242,894, entitled "DETECTING A PROBE-OFF EVENT IN A MEASUREMENT SYSTEM," filed Sep. 30, 2008, which is hereby incorporated by reference herein in its entirety, discusses suitable techniques for analyzing wavelet scalograms of the input signal to determine a probe off condition.

In one embodiment, alarm generator 630 may determine whether to trigger an alarm based at least in part on whether there is a significant noise event (e.g., in the form of an artifact) in the input signal. Any suitable technique for determining the existence of a significant noise event may be used. For example, U.S. patent application Ser. No. 12/245,336, entitled "SYSTEMS AND METHODS FOR ARTIFACT DETECTION IN SIGNALS," filed Oct. 3, 2008, which is hereby incorporated by reference herein in its entirety, discusses suitable techniques for identifying artifacts in an input signal by analyzing the signal's wavelet scalogram.

In one embodiment, alarm generator 630 may determine whether to trigger an alarm based at least in part on whether there is a state of low perfusion. Any suitable technique for determining the existence of a state of low perfusion. For example, U.S. patent application Ser. No. 12/249,325, entitled "LOW PERFUSION SIGNAL PROCESSING SYSTEMS AND METHODS," filed Oct. 10, 2008, which is hereby incorporated by reference herein in its entirety, discusses suitable techniques for determining the existence of a state of low perfusion.

In an embodiment, processing an $SpO_2$ signal to generate an alarm may include calculating a wavelet transform of the $SpO_2$ signal and then analyzing, in parallel, both the original $SpO_2$ signal and a scalogram based on the wavelet transform. For example, a system may calculate a wavelet transform of an $SpO_2$ signal and then analyze an RAP of the associated scalogram as well as the instantaneous slope of the original $SpO_2$ signal. Any combination of the $SpO_2$ signal features and scalogram features previously discussed may be used to generate an alarm based at least in part on an $SpO_2$ signal.

Figure 7:
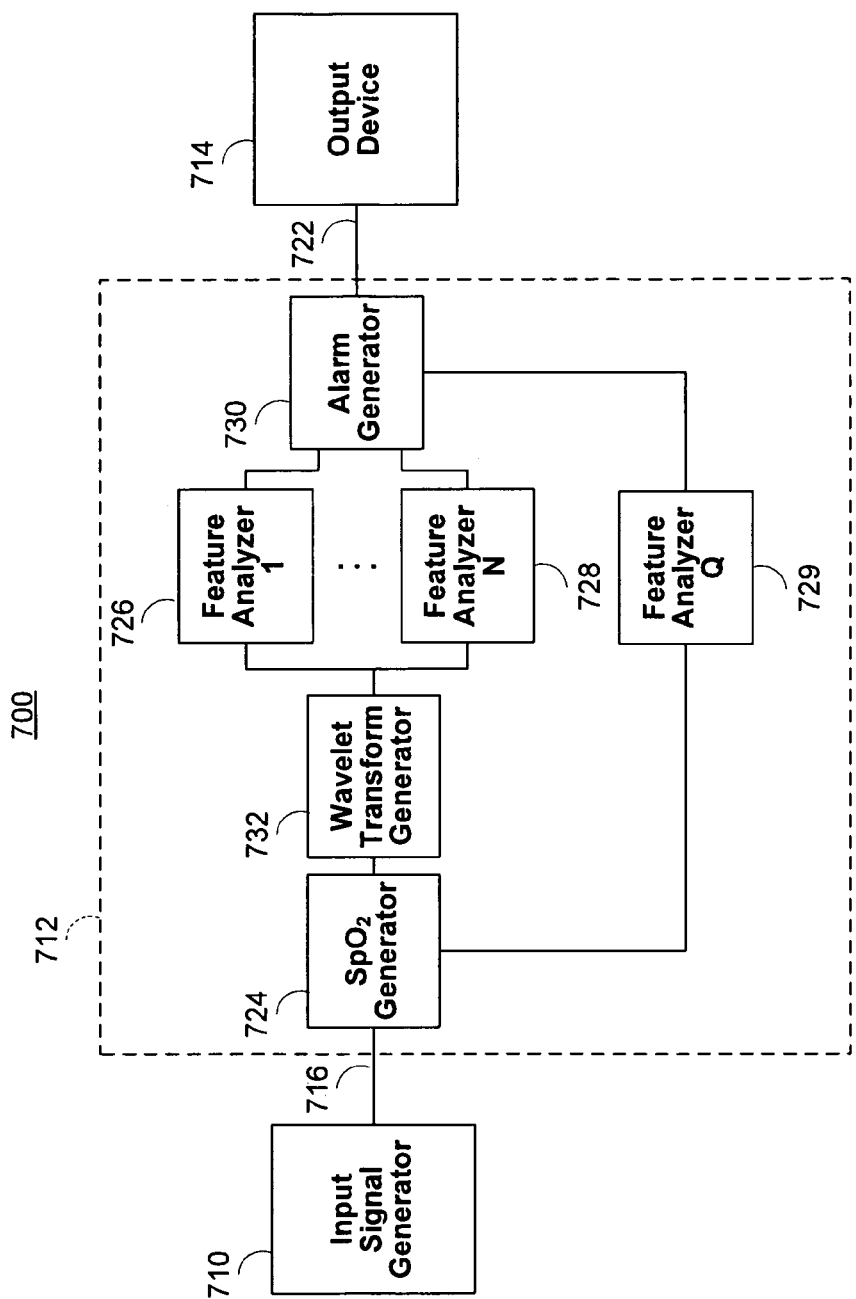
FIG. 7 is a block diagram of an illustrative continuous wavelet processing system in accordance with an embodiment.

FIG. 7 is an illustrative continuous wavelet processing system in accordance with an embodiment. In this embodiment, input signal generator 710 (or generator 410) may generate input signal 716 which may be a physiological signal (e.g., a PPG signal). Processor 712 (or processor 412) may analyze input signal 716 to generate alarm signal 722 that is read by output device 714 (or output device 414). Processor 712 may include an $SpO_2$ signal generator 724. $SpO_2$ signal generator 724 may generate an $SpO_2$ signal. As previously discussed, a variety of methods may be used to generate an $SpO_2$ signal. System 700 further includes wavelet transform generator 732 and feature analyzers 726, 728, and 729. Wavelet transform generator 732 may calculate the wavelet transform of the $SpO_2$ signal from $SpO_2$ signal generator 724 such that feature analyzers 726 and 728 may analyze the wavelet transform or a scalogram based on the wavelet transform. While only two feature analyzers are shown in FIG. 7, it is understood that a system may include any number of features analyzers for processing a scalogram in accordance with the disclosure. Feature analyzer 729 may analyze the original SpO$_2$ signal from SpO$_2$ signal generator 724. Feature analyzer 729 may analyze a characteristic in an SpO$_2$ signal (see, e.g., criteria processor 526 or criteria processor 528). While only one feature analyzer is shown in FIG. 7, it is understood that a system may include any number of feature analyzers for analyzing an original SpO$_2$ signal in accordance with the disclosure. The output of feature analyzer 729 may be provided to alarm generator 730 along with the output of feature analyzers 726 and 728. Accordingly, alarm generator 530 may generate an alarm based at least in part on one or more features of the SpO$_2$ signal and one or more features of a scalogram created from a wavelet transform of the SpO$_2$ signal. For example, one of feature analyzers 726 and 728 may analyze an RAP of the scalogram and feature analyzer 729 may analyze an instantaneous slope of the original SpO$_2$ signal so that alarm generator 530 may trigger an alarm if the RAP of the scalogram drops below a threshold and the instantaneous slope of the original SpO$_2$ signal is non-positive.

In an embodiment, processing an SpO$_2$ signal to generate an alarm may include extracting features from both the original SpO$_2$ signal and any syntactic processing, adaptive processing or Baysean analysis. For example, a system may analyze an instantaneous value or a moving average of an original SpO$_2$ signal while concurrently analyzing the SpO$_2$ signal using any suitable method for identifying trends or patterns.

It will be understood that the above embodiments, described primarily in terms of a PPG signal from which an SpO$_2$ signal or trend is derived, are merely illustrative. The principles of the present disclosure may be applied to any other suitable context. Such other contexts may include, for example, any other suitable biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

What is claimed is:

1. A method for determining whether to trigger an alarm, the method comprising:
   using a processor for:
      receiving an SpO$_2$ signal;
      performing a continuous wavelet transform of the SpO$_2$ signal to generate a scalogram;
      determining features of the scalogram; and
      determining whether to trigger an alarm based at least in part on the determined features.

2. The method of claim 1, wherein the features comprise features indicative of signal quality.

3. The method of claim 1, wherein the features comprise features indicative of a probe condition.

4. The method of claim 1, wherein the features comprise a moving average of the scalogram and a slope of the scalogram.

5. The method of claim 4, wherein the determining comprises triggering an alarm if the moving average of the scalogram is below a threshold and the slope of the scalogram is non-positive.

6. The method of claim 1, further comprising:
   determining a characteristic of the SpO$_2$ signal in parallel with the determining features of the scalogram, wherein the determining whether to trigger an alarm comprises determining whether to trigger an alarm based at least in part on the features and the characteristic.

7. The method of claim 6, wherein:
   the characteristic of the SpO$_2$ signal comprises a moving average of the SpO$_2$ signal; and
   the determining whether to trigger an alarm comprises determining whether to trigger an alarm based at least in part on whether the moving average of the SpO$_2$ signal is below a threshold.

8. The method of claim 1, further comprising:
   generating an alarm based at least in part on the determining whether to trigger an alarm.

9. A system capable of determining whether to trigger an alarm, the system comprising:
   a sensor capable of generating a photoplethysmograph (PPG) signal;
   an SpO$_2$ signal generator coupled to the sensor and capable of generating an SpO$_2$ signal based at least in part on the PPG signal;
   a wavelet transform generator coupled to the SpO$_2$ signal generator and capable of performing a continuous wavelet transform of the SpO$_2$ signal to generate a scalogram;
   a plurality of feature analyzers, each feature analyzer coupled to the wavelet transform generator and capable of determining a feature of the scalogram and providing an output; and
   an alarm generator coupled to the outputs of the plurality of feature analyzers and capable of triggering an alarm based at least in part on the outputs.

10. The system of claim 9, wherein the features comprise features indicative of signal quality.

11. The system of claim 9, wherein the features comprise features indicative of a probe condition.

12. The system of claim 9, wherein the plurality of feature analyzers comprises:
   a first feature analyzer capable of determining a moving average of the scalogram; and
   a second feature analyzer capable of determining a slope of the scalogram.

13. The system of claim 12, wherein the alarm generator is capable of generating an alarm if the output of the first feature analyzer indicates that the moving average of the scalogram is below a threshold and the output of the second feature analyzer indicates that the slope of the scalogram is non-positive.

14. The system of claim 9, further comprising a criteria processor coupled to the SpO$_2$ signal generator and capable of determining at least one characteristic of the SpO$_2$ signal and providing an output, wherein the alarm generator is coupled to the output of the criteria processor and capable of determining whether to trigger an alarm based at least in part on the output of the criteria processor.

15. The system of claim 14, wherein:
   the plurality of feature analyzers comprises a first feature analyzer capable of determining a slope of the scalogram;
   the criteria processor is capable of determining a moving average of the SpO$_2$ signal;
   and the alarm generator is capable of generating an alarm if the output of the criteria processor indicates that the moving average of the SpO$_2$ signal is below a threshold and the output of the first feature analyzer indicates that the slope of the scalogram is non-positive.

16. Non-transitory computer-readable medium for use in determining whether to trigger an alarm, the non-transitory computer-readable medium having computer program instructions recorded thereon for:
   receiving an SpO$_2$ signal;
   performing a continuous wavelet transform of the SpO$_2$ signal to generate a scalogram;

determining features of the scalogram; and determining whether to trigger an alarm based at least in part on the determined features.

17. The non-transitory computer-readable medium of claim 16 having further computer program instructions recorded thereon for:

determining a characteristic of the $SpO_2$ signal in parallel with the determining features of the scalogram, wherein the determining whether to trigger an alarm comprises determining whether to trigger an alarm based at least in part on the features and the characteristic.

* * * * *